US00PP24329P2

(12) United States Plant Patent
Korlipara

(10) Patent No.: US PP24,329 P2
(45) Date of Patent: Mar. 18, 2014

(54) *ECHINACEA* PLANT NAMED 'GLOWING DREAM'

(50) Latin Name: ***Echinacea* spp.**
Varietal Denomination: Glowing Dream

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 56 days.

(21) Appl. No.: 13/573,330

(22) Filed: Sep. 11, 2012

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Glowing Dream' characterized by an amazing number of inflorescences starting in the first season, very long bloom time with excellent rebloom, a very compact habit, deep coral pink ray florets surrounding dark cones, numerous, strong dark stems, and excellent vigor.

1 Drawing Sheet

Botanical denomination: *Echinacea* spp.
Variety designation: 'Glowing Dream'.

BACKGROUND OF THE INVENTION

The present invention relates to a new and distinct cultivar of *Echinacea* and given the cultivar name 'Glowing Dream'. *Echinacea* is in the family *Asteraceae*. The new cultivar is part of a planned breeding program for a landscape series with compact habits and profuse inflorescences. The exact parents of this selection are unknown, unnamed, proprietary interspecific hybrids of *Echinacea paradoxa, Echinacea purpurea*, and *Echinacea tennesseensis*. This cultivar was selected for its glowing coral pink flowers.

Compared to *Echinacea* 'Raspberry Tart' (U.S. Plant Pat. No. 18,933), the new cultivar has ray florets, more basal crowns, and is much longer blooming.

Compared to *Echinacea* 'Amazing Dream' (U.S. patent application Ser. No. 12/931,221), the new cultivar has coral pink rather than deep pink ray florets.

This new *Echinacea* cultivar is uniquely distinguished by:

1. an amazing number of inflorescences starting in the first season,
2. very long bloom time with excellent rebloom,
3. very compact habit,
4. deep coral pink ray florets surrounding dark cones,
5. numerous, strong dark stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences and habit of *Echinacea* 'Glowing Dream' as a two-year-old growing in the garden in full sun in mid-July in Canby, Oreg.

DETAILED PLANT DESCRIPTION

The following is a detailed description of the new *Echinacea* cultivar based on observations of two-year-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type*.—Herbaceous perennial.
*Hardiness*.—USDA Zones 4 to 9.
*Size*.—Grows to about 35 cm wide and 40 cm tall to top of inflorescences.
*Form*.—Basal clump, with about 30 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 2 inflorescences per stem.
*Size*.—To 37 cm tall to a terminal inflorescence and 6.5 mm wide at base.
*Internode length*.—2 cm to 5 cm.
*Surface texture*.—Strigose.
*Color*.—Yellow Green 145A at the base blending to Brown 200C near flower.

Leaf:

*Type*.—Simple.

*Shape*.—Lanceolate.

*Arrangement*.—Alternate.

*Blade size*.—Grows to 11 cm long and 2.9 cm wide.

*Margins*.—Entire.

*Apex*.—Acuminate.

*Base*.—Attenuate.

*Surface texture*.—Strigose on both sides.

*Venation*.—Pinnate, Yellow Green 145B on both sides.

*Color*.—Topside Green 137A, bottom side Green 137B.

*Petiole description*.—On lowermost leaves only, clasping, grows to 9.5 cm long and 3 mm wide, scabrous, narrow leafy edges which fold upwards, Yellow Green 145B on both sides except leafy edges, Green 137B.

Inflorescence:

*Type*.—Composite on terminal stalked heads.

*Number of flowering stems from the ground*.—About 30.

*Flowering stem*.—Grows to 37 cm tall from the base of the plant to the terminal inflorescence and can grow to 13.5 cm long from the top stem leaf to the base of an inflorescence; unbranched to branched, with 1 to 2 inflorescences per stem; diameter growing to 9 mm wide near the inflorescence; strigose; Yellow Green 145A at the base blending to Brown 200C near flower.

*Size*.—Grows to 8.5 cm wide and 4 cm deep as disc enlarges.

*Form*.—Ray florets held slightly reflexed, mature disc is conic.

*Immature inflorescence*.—Grows to 2.5 cm wide and 2.5 cm deep, ray florets held upright at 10 degrees from the vertical and rolled up so only the back color shows, Greyed Purple 186A, disc color Greyed Purple 187A.

*Ray florets*.—Without pistil or stamen, about 20, grow to 4 mm long and 10 mm wide, elliptic to oblanceolate with the tip two to three-toothed (each acute), entire margins, base attenuate, glabrous on both sides; topside between Red Purple 53A and Red 53A; bottom side Red Purple 59C, old flowers topside Red Purple 58A bottom side Red Purple 59C.

*Disc*.—Flat becoming conic, becoming 32 mm deep and 29 mm wide with maturity, Greyed Purple 187A in background with bracts Orange 25A.

*Disc florets*.—About 400 in number, each with 1 pistil and 4 stamen, grow to 11 mm long and 1.5 mm wide, each with one persistent, very stiff linear bract (12 mm long with the top 1 mm Greyed Purple 187A to 2 mm colored Orange 25A to 4 mm Yellow Green 146B to White NN155A on bottom); corolla 5 mm long and 1.5 mm wide, tubular, 5 lobed, glabrous, base Greyed Purple 186B to middle Green 146A to lobes Greyed Purple 187A; pistil 11 mm long, ovary 4 mm long, White NN155D with top Yellow Green 144A, style 6 mm long Yellow Green 145D, 2-branched stigma spreading 2 mm wide, Greyed Purple 187A; stamen 4 mm long, filaments 2 mm long and White NN155B, anthers 2 mm long and Greyed Purple 187A, pollen Yellow Orange 15A.

*Phyllaries*.—In 4 leafy series, area grows to 25 mm wide and 10 mm deep, lobes lanceolate in shape, reflexed, grow to 12 mm long and 2 mm wide, Yellow Green 147B, margins strigose, tip acute, strigose on both sides.

*Receptacle*.—Grows to 11 mm wide and 22 mm deep, White NN155B.

*Bloom period*.—July through October in Canby, Oreg.

*Fragrance*.—Floral, sweet.

*Lastingness*.—Each inflorescence lasts about two weeks in Canby, Oreg.

Seeds: 3 mm long and 2.5 mm wide, oval, Brown 200C.

*Fertility*.—Good.

Disease and pests: No pests or diseases have been observed on plants grown under commercial conditions in Canby, Oreg. No resistances are known.

I claim:

1. A new and distinct *Echinacea* plant as herein illustrated and described.

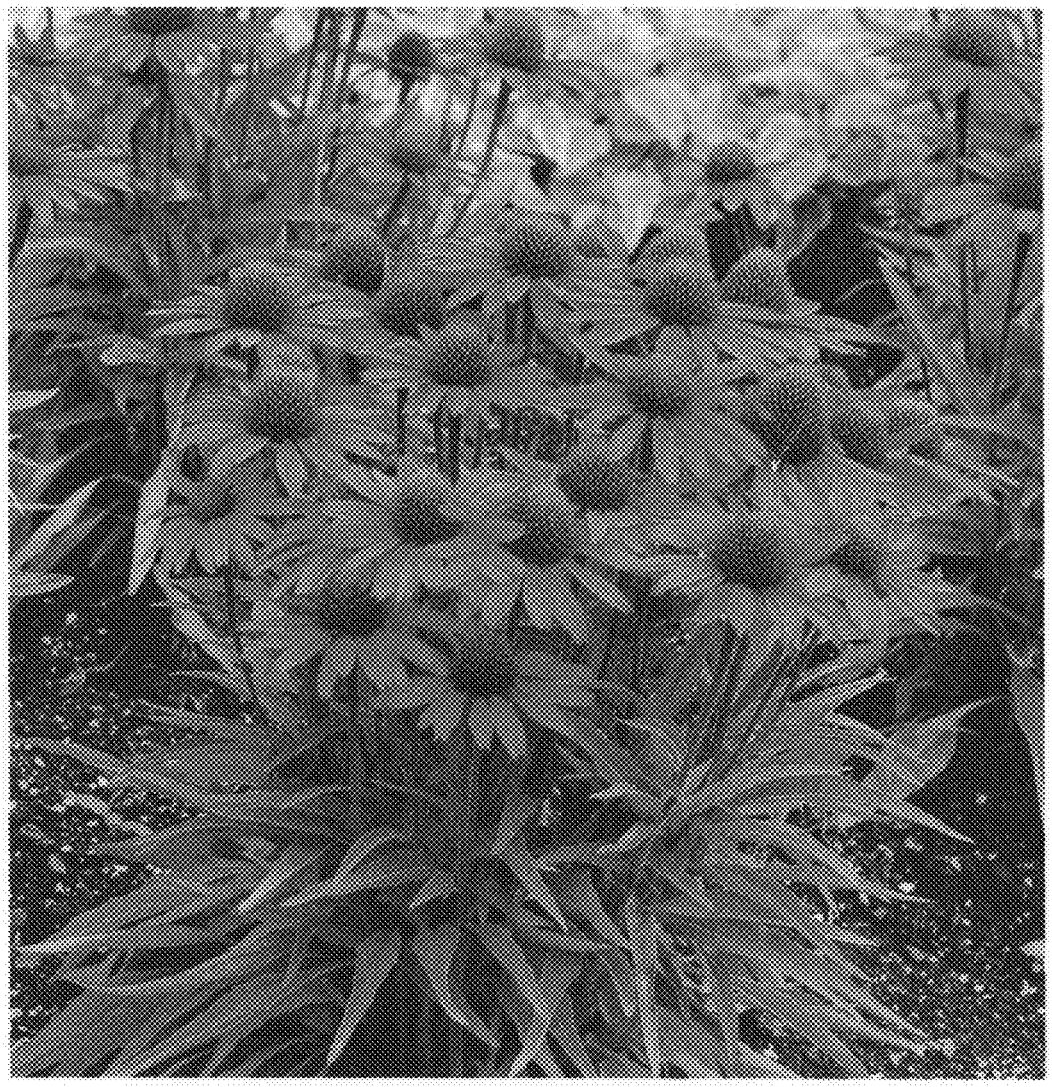

* * * * *